US 6,878,117 B1

(12) United States Patent
Watrous

(10) Patent No.: US 6,878,117 B1
(45) Date of Patent: Apr. 12, 2005

(54) HANDHELD SENSOR FOR ACOUSTIC DATA ACQUISITION

(75) Inventor: Raymond L. Watrous, Belle Meade, NJ (US)

(73) Assignee: Zargis Medical Corp., Princeton, NJ (US)

(*) Notice: Subject to any disclaimer, the term of this patent is extended or adjusted under 35 U.S.C. 154(b) by 385 days.

(21) Appl. No.: 09/670,053

(22) Filed: Sep. 25, 2000

Related U.S. Application Data

(60) Provisional application No. 60/156,725, filed on Sep. 30, 1999, and provisional application No. 60/156,601, filed on Sep. 29, 1999.

(51) Int. Cl.$^7$ .............................................. A61B 5/02
(52) U.S. Cl. ........................................ 600/528; 128/903
(58) Field of Search ................................ 181/131, 137; 600/495, 528, 453–456; 128/903

(56) References Cited

U.S. PATENT DOCUMENTS

| | | | | |
|---|---|---|---|---|
| 3,858,575 A | | 1/1975 | Rose ...................... 128/2.05 S |
| 3,951,230 A | * | 4/1976 | Littman ..................... 181/131 |
| 4,170,717 A | | 10/1979 | Walshe ........................... 179/1 |
| 4,254,302 A | | 3/1981 | Walshe ........................... 179/1 |
| 4,428,381 A | | 1/1984 | Hepp ........................... 128/715 |
| 4,458,693 A | | 7/1984 | Badzinski et al. .......... 128/715 |
| 4,534,058 A | | 8/1985 | Hower ........................... 381/67 |
| 4,594,731 A | | 6/1986 | Lewkowicz .................. 381/67 |
| 4,598,417 A | | 7/1986 | Deno ............................ 381/67 |
| 4,618,986 A | | 10/1986 | Hower .......................... 381/67 |
| 4,723,555 A | | 2/1988 | Shue .......................... 128/715 |
| 4,821,731 A | * | 4/1989 | Martinelli et al. .......... 600/463 |
| 5,218,969 A | * | 6/1993 | Bredesen et al. ........... 600/523 |
| 5,343,869 A | * | 9/1994 | Pross et al. ................. 128/700 |
| 5,347,583 A | | 9/1994 | Diecken et al. .............. 381/67 |
| 5,367,575 A | | 11/1994 | Diecken et al. .............. 381/67 |
| 5,467,775 A | | 11/1995 | Callahan ..................... 128/715 |
| 5,557,681 A | | 9/1996 | Thomasson .................. 381/67 |
| 5,602,924 A | | 2/1997 | Durand ........................ 381/67 |
| 5,810,008 A | * | 9/1998 | Dehel et al. ................ 128/916 |
| 5,885,222 A | | 3/1999 | Kassal et al. ............... 600/528 |
| 6,002,777 A | | 12/1999 | Grasfield ...................... 381/67 |
| 6,005,951 A | | 12/1999 | Grasfield ...................... 381/67 |
| 6,026,170 A | | 2/2000 | Diecken et al. .............. 381/67 |
| 6,134,331 A | | 10/2000 | Baekgaard ................... 381/67 |
| 6,282,455 B1 | * | 8/2001 | Eugdahl ....................... 700/83 |

FOREIGN PATENT DOCUMENTS

| WO | WO 94/09702 | 5/1994 |
|---|---|---|
| WO | WO 96/13212 | 5/1996 |

* cited by examiner

*Primary Examiner*—Francis J. Jaworski
(74) *Attorney, Agent, or Firm*—Donald B. Paschburg

(57) ABSTRACT

An apparatus according to an embodiment of the present invention is provided for sensing acoustic signals. The apparatus includes a housing having an apertured posterior member, a sensing unit extending through the apertured posterior member for interfacing by contact with a patient, a cursor control for positioning a cursor on a display, the display located anteriorially on the housing, a button for fixing a position of the cursor in the display, indicating the position on the housing with respect to the patient, and a circuit for causing the cursor to move about the display in response to the cursor control, and for transmitting the acoustic signal.

19 Claims, 3 Drawing Sheets

HANDHELD SENSOR FOR ACOUSTIC DATA ACQUISITION

This a non-provisional application claiming the benefit of provisional application Ser. No. 60/156,725, filed Sep. 30, 1999, incorporating by reference the provisional patent application, Ser. No. 60/156,601, entitled "A MultiModal Cardiac Diagnostic Decision Support System for Echocardiography Referral," filed on Sep. 29, 1999. The non-provisional application entitled "MultiModal Cardiac Diagnostic Decision Support System and Method", claiming the benefit of the provisional patent application, Ser. No. 60/156,601, is filed concurrently with the present application, and is incorporated by reference herein.

BACKGROUND OF THE INVENTION

1. Field of the Invention

The present invention is directed to a hand held sensor for acoustic data acquisition in medical diagnosis, and more particularly, a sensor having a cursor control for a position-indicating display.

2. Description of Related Art

The traditional method of acoustic diagnosis in medicine surrounded the use of stethoscopes, in particular, for the diagnosis of cardiovascular disease. However, stethoscopes have limited functionality, both in design and implementation. The stethoscope itself transfers only a small fraction of the acoustic signal at the chest surface to the listener's ears, and filters the cardiac acoustic signal in the process.

In particular, with respect to auscultation of the heart, much of the signal energy in many heart sounds is below the threshold of human hearing. This situation is compounded by the degradation of the listener's hearing which can be associated with, for example, age and/or exposure to excessive noise. Auscultation also relies on correctly determining which of the primary heart sounds correspond with the systolic and diastolic phase of the heart, which is made more difficult when the systolic and diastolic intervals are more equal, typically at elevated heart rates. Auscultation also relies on detecting the correct sequence of brief events occurring close in time, something that is difficult for human listeners.

Learning auscultation is also difficult because diagnostic instructional manuals rely on subjective descriptions of heart sounds, which need practice to appreciate. Furthermore, following decisions by certain medical coverage providers not to reimburse for phonocardiography, the practice and teaching of the clinical skill of auscultation of the heart has declined among physicians. Recent tests have demonstrated that physicians can identify, reliably, only a small number of standard heart sounds and murmurs. Consequently, serious heart murmurs in many patients go undetected by physicians.

In addition, the decline in auscultation skills has led to an over-reliance on echocardiography, resulting in a large number of unnecessary and expensive diagnostic studies. As a result, reimbursement for echocardiography has come under scrutiny by Medicare.

Therefore, a need exists for an acoustic data acquisition device for use in medical diagnosis.

SUMMARY OF THE INVENTION

An apparatus according to an embodiment of the present invention is provided for sensing acoustic signals. The apparatus includes a housing having an apertured posterior member, a sensing unit extending through the apertured posterior member for interfacing by contact with a patient, a cursor control for positioning a cursor on a display, the display located anteriorially on the housing, a button for fixing a position of the cursor in the display, indicating the position on the housing with respect to the patient, and a circuit for causing the cursor to move about the display in response to the cursor control, and for transmitting the acoustic signal.

According to one embodiment of the present invention, the sensing unit is passive. The sensing unit is mounted to the pod by a mounting spring for reducing a motion artifact in the acoustic signal. The cursor control, according to another embodiment, is a rocker switch having two axes of motion. The acoustic signal is transmitted by a cable or a wireless transmitter to a data processing system. The circuit includes a telemetry circuit for monitoring pod position relative to the patient and a pre-amplifier circuit for amplifying the acoustic signal.

In another embodiment of the present invention, an apparatus for sensing an acoustic signal is disclosed including a housing having an apertured posterior member, a sensing unit for interfacing by contact with a patient and capturing the acoustic signal, and a telemetry sensor for indicating the position of the housing with respect to the patient.

The sensing unit is passive. The sensing unit is supported by a mounting spring according to one embodiment, for reducing a motion artifact in the acoustic signal. The sensing unit extends through the apertured posterior member. In another embodiment the sensing unit is flush mounted in the housing. The acoustic signal is transmitted by a cable or a wireless transmitter to a data processing system.

According to yet another embodiment, an apparatus for generating an electrical signal representative of an acoustic signal of a cardiovascular system is presented. The apparatus includes a sensing unit for detecting the acoustic signal and converting the acoustic signal to the electrical signal, a preamplifier for amplifying the electrical signal, and a telemetry unit for transmitting positional data and the electrical signal to a data processing system. The apparatus also includes a liquid crystal display located anteriorly on a pod housing the sensor, the preamplifier, and the telemetry unit, a rocker switch for positioning a cursor in the display, indicating a position of the sensing unit with respect to a patient, and a contoured switch for fixing the position of the cursor on the display. The positioning of the cursor is converted from an analog position of the rocker switch to a digital signal by a cursor control circuit.

The sensing unit is supported by a mounting spring for reducing a motion artifact in the acoustic signal and extends through the apertured posterior member. In another embodiment of the present invention, the sensing unit is flush mounted in the housing.

BRIEF DESCRIPTION OF THE DRAWINGS

Preferred embodiments of the present invention will be described below in more detail, with reference to the accompanying drawings.

DETAILED DESCRIPTION OF PREFERRED EMBODIMENTS

Figure 1A:
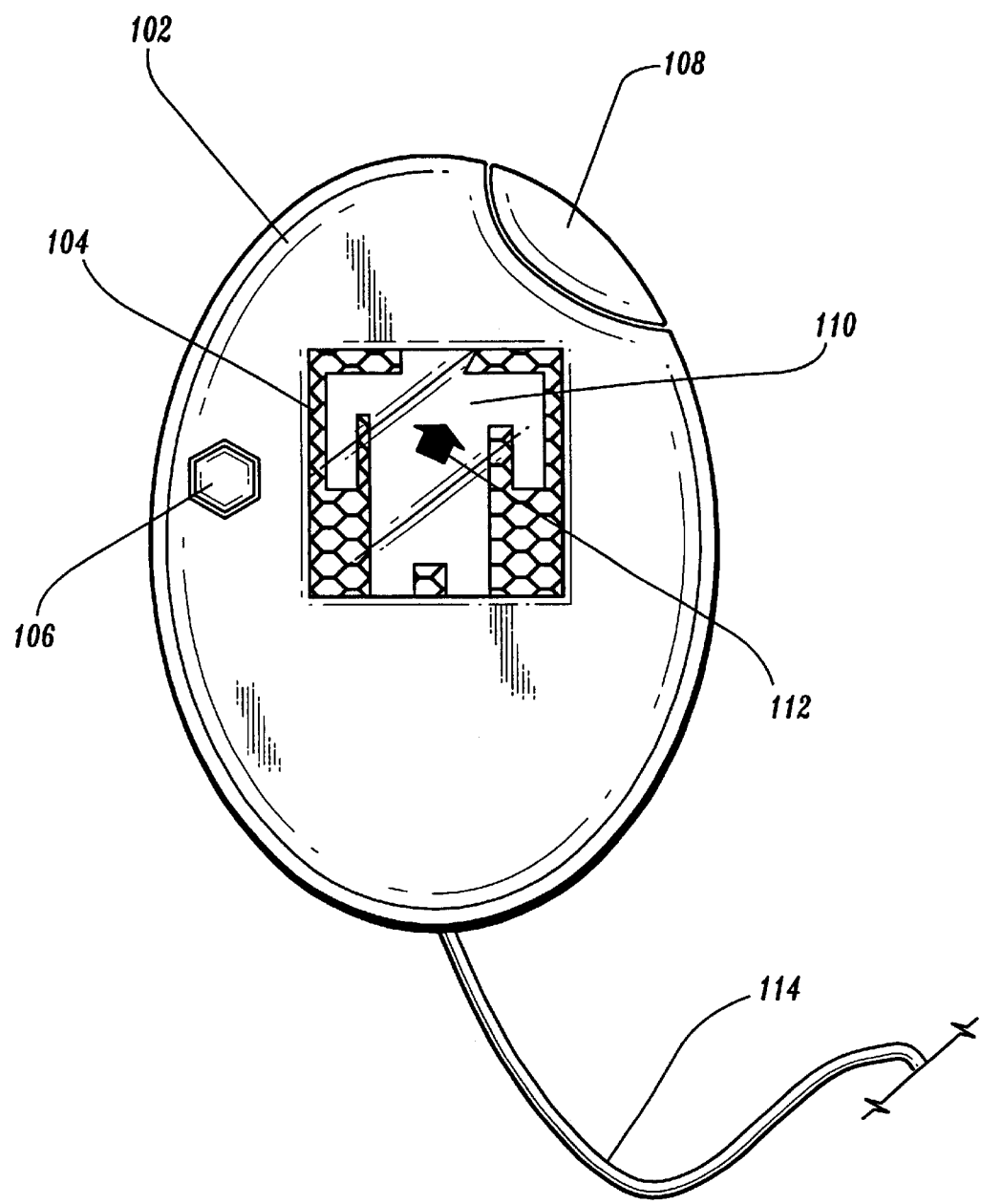
FIG. 1A is a top-down view of an acoustic sensing device according to one embodiment of the present invention.
Figure 1B:
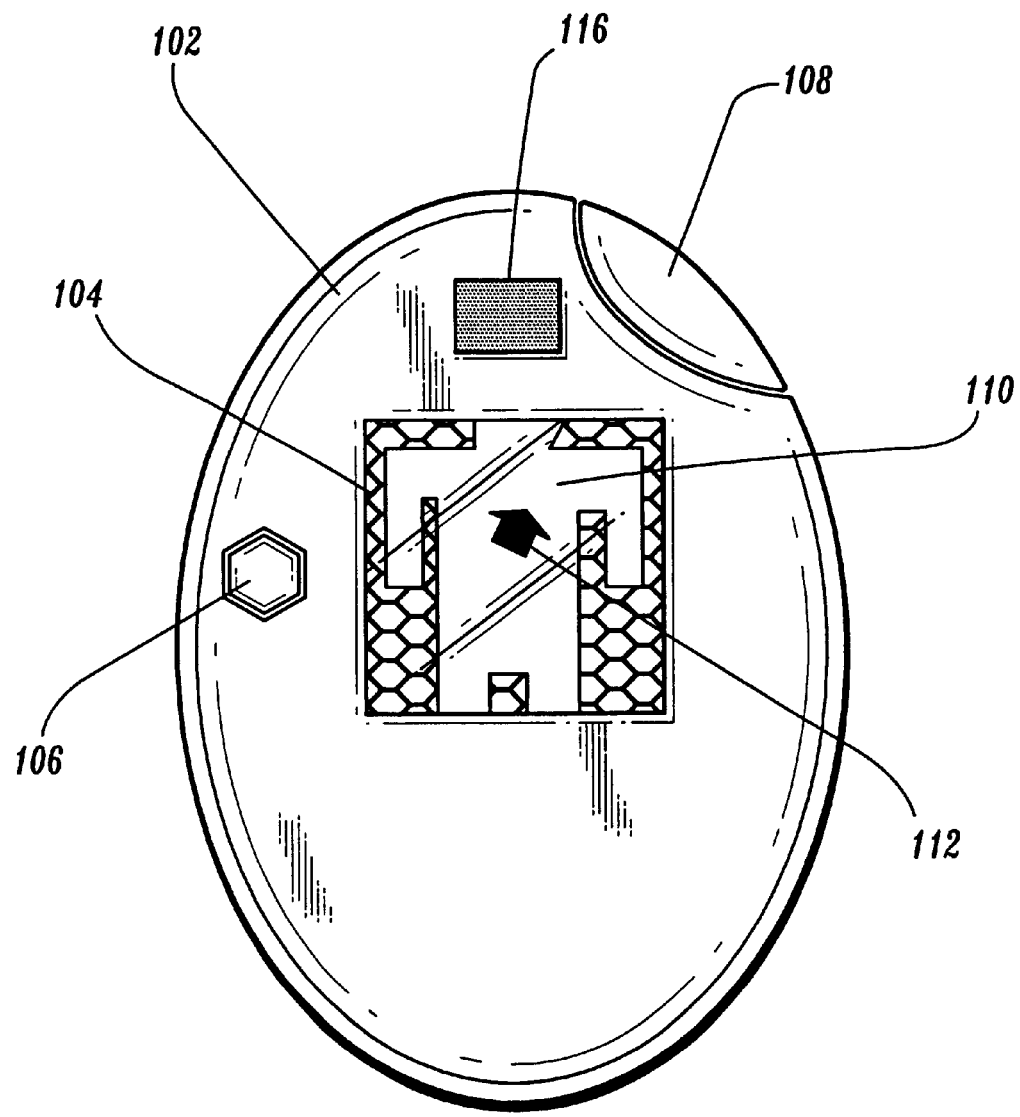
FIG. 1B is a top-down view of an acoustic sensing device having an infrared port according to another embodiment of the present invention.
Figure 2:
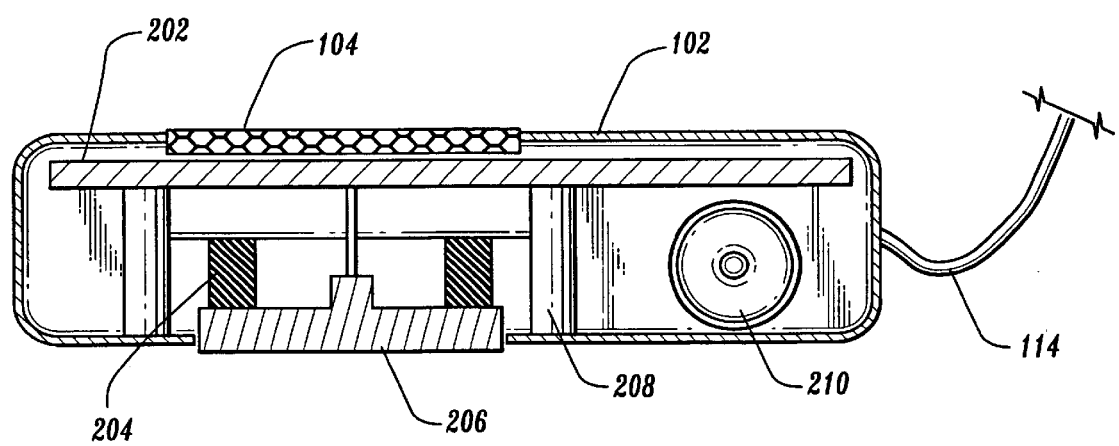
FIG. 2 is an exposed side view of an acoustic sensing device according to yet another embodiment of the present invention.

Referring to FIG. 1, a hand-held device, or "pod" 102, according to one embodiment of the present invention, incorporates an acoustic sensing element 206 (shown in FIG. 2) for capturing sound waves, and a position-indicating display 104 for displaying telemetry data.

The acoustic sensing element 206 extends partially from an aperture on the bottom of the pod. The sensing element is spring-mounted 204 in order to apply moderate and controlled pressure against the chest or back of a patient. The spring mounting gives the sensing element a measure of mechanical independence from the sensor pod to reduce motion artifacts. Alternatively, mounting apparatus such as rubber mounts, leaf-springs, coil springs, a pivot joint, fluids, jells, etc., can be used alone or in combination to support the sensing element. In another embodiment of the present invention, the sensor is in a static position, flush with the bottom of the pod, where the pod and sensor form a continuous surface. Further, an acoustically conductive lubricating agent may be applied to the skin of the patient to facilitate acoustic interfacing between the sensor and the patient.

The pod 102 houses a printed-circuit board 202, supported by studs 208. Electronics mounted on the printed-circuit board include preamplifier circuitry, cursor control circuitry, telemetry circuitry, and/or other circuitry for processing signals to/from the sensor 206. In another embodiment of the present invention, the electronics include the preamplifier circuitry and cursor control circuitry. Alternatively, the electronics or another control broad can be located external to the pod 102, connected to the sensor via a cable 114.

The pod 102 also houses a battery 210 for providing power to the electronics. The power can also be provided via the cable 114 connecting the pod 102 to a diagnostic support or data processing system.

A planar liquid crystal display (LCD) 104 is mounted on the surface of the pod 102. A rocker switch 106, preferably with two axes of motion, is flush-mounted on the left side of the pod 102, and a contoured switch 108 is embedded in the upper right surface of the pod 102. The rocker switch 106 controls the position of a visible cursor 112 that registers the sensor position on an outline of the thorax 110, which is overlaid on the LCD 104. Movement of the rocker switch 106 is translated into movement of the cursor on the LCD 104 by the cursor control circuitry. The contoured switch 108 may be used to signal that the sensor is in the desired position and that the sensor position is correctly registered on the LCD 104. Through the use of the LCD 104, rocker switch 106, and contoured switch 108, the data acquisition and processing system can acquire positional information. The positional information preferably includes the position of the sensor relative to the patient and/or elements of the patient's cardiovascular system. One with ordinary skill in the art would recognize, in light of the present invention, that other control mechanisms are possible, for example, a joystick, touch-pad, trackball, or scrolling wheel.

The acoustic signal is pre-amplified by the pre-amplifying circuitry, while the positional information is processed by the telemetry circuitry. The amplified acoustic signal and processed positional information can then be transmitted to the data processing system either by a cable, or remotely using wireless technology. The telemetry circuitry preferably transmits the acoustic signal and positional data. A wireless connection using, for example, wireless application protocol (WAP) or infrared (IR), may be made using a data transmission device, such as an antenna or IR port 116. Other transmission protocols are contemplated by the present invention.

Having described embodiments for a handheld sensor for acoustic data acquisition, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set for in the appended claims.

What is claimed is:

1. An apparatus for sensing an acoustic signal, comprising:
   a housing having an apertured posterior member;
   a sensing unit extending through the apertured posterior member for interfacing by contact with a patient;
   a cursor control for positioning a cursor on a display, the display located anteriorially on the housing;
   a button for fixing a position of the cursor in the display, indicating the position of the housing with respect to the patient; and
   a circuit for causing the cursor to move about the display in response to the cursor control, and for transmitting the acoustic signal.

2. The apparatus of claim 1, wherein the sensing unit is passive.

3. The apparatus of claim 1, wherein the sensing unit is mounted to a pod by a mounting spring for reducing a motion artifact in the acoustic signal.

4. The apparatus of claim 1, wherein the cursor control is a rocker switch having two axes of motion.

5. The apparatus of claim 1, wherein the acoustic signal is transmitted via one of a cable and a wireless transmitter to a data processing system.

6. The apparatus of claim 1, wherein the circuit further comprises a pre-amplifier circuit for amplifying the acoustic signal.

7. An apparatus for sensing an acoustic signal comprising:
   a housing having an apertured posterior member;
   a sensing unit for interfacing by contact with a patient and capturing the acoustic signal, wherein the sensing unit is supported by a mounting apparatus for reducing a motion artifact in the acoustic signal, wherein the mounting apparatus is connected to the housing; and
   a telemetry sensor for indicating a position of the housing with respect to the patient.

8. The apparatus of claim 7, wherein the sensing unit is passive.

9. The apparatus of claim 8, wherein the sensing unit is flush mounted with the housing.

10. The apparatus of claim 7, wherein the mounting apparatus is one of a spring, and a rubber mount.

11. The apparatus of claim 10, wherein the sensing unit extends through the apertured posterior member.

12. The apparatus of claim 7, wherein the acoustic signal is transmitted via one of a cable and a wireless transmitter to a data processing system.

13. An apparatus for generating an electrical signal representative of an acoustic signal of a cardiovascular system comprising:

a sensing unit for detecting the acoustic signal and converting the acoustic signal to the electrical signal, wherein the sensing unit is supported by a mounting apparatus for reducing a motion artifact in the acoustic signal, wherein the mounting apparatus is connected to a pod housing;

a preamplifier for amplifying the electrical signal; and a telemetry unit for transmitting positional data and the electrical signal to a data processing system.

14. The apparatus of claim 13, further comprising:

a liquid crystal display located anteriorly on the pod housing the sensor, the pre-amplifier, and the telemetry unit, a rocker switch for positioning a cursor in the display, indicating a position of the sensing unit with respect to a patient; and contoured switch for fixing the position of the cursor on the display.

15. The apparatus of claim 14, wherein the positioning of the cursor is converted from an analog position of the rocker switch to a digital signal by a cursor control circuit.

16. The apparatus of claim 13, wherein the mounting apparatus is one of a spring, and a rubber mount.

17. The apparatus of claim 14, wherein the sensing unit extends through an apertured posterior member of the pod housing.

18. The apparatus of claim 14, wherein the sensing unit is flush mounted in the housing.

19. An apparatus for generating an electrical signal representative of an acoustic signal of a cardiovascular system comprising:

a sensing unit for detecting the acoustic signal and converting the acoustic signal to the electrical signal;

a preamplifier for amplifying the electrical signal;

a telemetry unit for transmitting positional data and the electrical signal to a data processing system;

a liquid crystal display located anteriorly on a pod housing the sensor, the preamplifier, and the telemetry unit;

a rocker switch for positioning a cursor in the display, indicating a position of the sensing unit with respect to a patient; and a contoured switch for fixing the position of the cursor on the display.

* * * * *